United States Patent [19]

Kim et al.

[11] Patent Number: 5,512,560
[45] Date of Patent: Apr. 30, 1996

[54] CONFORMATIONALLY RESTRICTED HIV-1 PROTEASE INHIBITORS

[75] Inventors: Byeong M. Kim, Hatfield; Joseph P. Vacca, Telford, both of Pa.

[73] Assignee: Merck & Co., Inc., Rahway, N.J.

[21] Appl. No.: 219,572

[22] Filed: Mar. 29, 1994

[51] Int. Cl.$^6$ .................. A61K 31/445; A61K 31/47; C07D 211/40; C07D 207/273

[52] U.S. Cl. .................. 514/210; 514/314; 514/317; 514/319; 514/320; 514/324; 514/326; 514/327; 514/422; 514/424; 546/164; 546/192; 546/202; 546/206; 546/207; 546/213; 546/217; 548/518; 548/525; 548/544; 548/952

[58] Field of Search .................. 548/518, 525, 548/544, 952; 546/164, 192, 202, 206, 207, 213, 214, 217; 514/210, 314, 317, 319, 320, 324, 326, 327, 422, 424

[56] References Cited

PUBLICATIONS

Kohl et al., *Proc. Natl. Acad. Sci.*, vol. 85, p. 4686 (1988).
Ratner et al., *Nature*, vol. 313, p. 297, (1985).
Toh et al., *EMBO.*, vol. 4, p. 1267 (1985).

*Primary Examiner*—C. Warren Ivy
*Assistant Examiner*—Raymond Covington
*Attorney, Agent, or Firm*—Roy D. Meredith; Jack L. Tribble

[57] ABSTRACT

HIV protease inhibitors containing hydroxypyrrolidine or hydroxypiperidine with one or more basic amines are disclosed.

16 Claims, No Drawings

CONFORMATIONALLY RESTRICTED HIV-1 PROTEASE INHIBITORS

The present invention is concerned with compounds which inhibit the protease encoded by human immunodeficiency virus (HIV). The compounds, or pharmaceutically acceptable salts thereof, are of value in the prevention of infection by HIV, the treatment of infection by HIV and the treatment of the resulting acquired immune deficiency syndrome (AIDS).

The present invention also relates to pharmaceutical compositions containing the compounds and to a method of use of the present compounds and other agents for the treatment of AIDS & viral infection by HIV.

BACKGROUND OF THE INVENTION

A retrovirus designated human immunodeficiency virus (HIV) is the etiological agent of tile complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E., et. al., *Proc. Natl. Acad, Sci. USA*, 85, 4686 (1988), demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

Nucleotide sequencing of HIV shows the presence of a pol gene in one open reading frame [Ratner, L. et al., *Nature*, 313, 277(1985)]. Amino acid sequence homology provides evidence that the pol sequence encodes reverse transcriptase, an endonuclease and an HIV protease [Toh, H. et al., *EMBO J*. 4, 1267 (1985); Power, M. D. et al., *Science*, 231, 1567 (1986); Pearl, L. H. et al., *Nature* 329, 351 (1987)]. Applicants demonstrate that the compounds of this invention are inhibitors of HIV protease.

The compounds of the present invention contain hydroxypyrrolidine or hydroxypiperidine with one or more basic amines. The particular advantages of these compounds are increased potency due to the restricted bioactive conformation.

BRIEF DESCRIPTION OF THE INVENTION

Compounds of Formula I, as herein defined, are disclosed. These compounds are useful in the inhibition of HIV protease, the prevention of infection by HIV, the treatment of infection by HIV and in the treatment of AIDS, either as compounds, pharmaceutically acceptable salts, hydrates or esters, pharmaceutical composition ingredients, whether or not in combination with other antivirals, immunomodulators, antibiotics or vaccines. Methods of treating AIDS, methods of preventing infection by HIV, and methods of treating infection by HIV are also disclosed.

| Designation | |
|---|---|
| | Protecting Group |
| BOC (Boc) | t-butyloxycarbonyl |
| CBZ (Cbz) | benzyloxycarbonyl(carbobenzoxy) |
| TBS (TBDMS) | t-butyl-dimethylsilyl |
| | Activating Group |
| HBT(HOBT or HOBt) | 1-hydroxybenzotriazole hydrate |
| | Coupling Reagent |
| BOP reagent | benzotriazol-1-yloxytris-(dimethylamino)phosphonium hexafluorophosphate |
| BOP-Cl | bis(2-oxo-3-oxazolidinyl)phosphinic chloride |
| EDC | 1-ethyl-3-(3-dimethylaminopropyl)carbodiimide hydrochloride |
| | Other |
| (BOC)$_2$O (BOC$_2$O) | di-t-butyl dicarbonate |
| n-Bu$_4$N+F− | tetrabutyl ammonium fluoride |
| nBuLi (n-Buli) | n-butyllithium |
| DMF | dimethylformamide |
| Et$_3$N | triethylamine |
| EtOAc | ethyl acetate |
| TFA | trifluoroacetic acid |
| DMAP | dimethylaminopyridine |
| DME | dimethoxyethane |
| LDA | lithium diisopropylamide |
| THF | tetrahydrofuran |
| | Amino Acid |
| Ile | L-isoleucine |
| Val | L-valine |

DETAILED DESCRIPTION OF THE INVENTION AND PREFERRED EMBODIMENTS

This invention is concerned with the compounds of Formula I, combinations thereof, or pharmaceutically acceptable salts thereof, in the inhibition of HIV protease, the prevention of infection by HIV, the treatment of infection by HIV and in the treatment of the resulting acquired immune deficiency syndrome (AIDS). Compounds of Formula I are defined as follows:

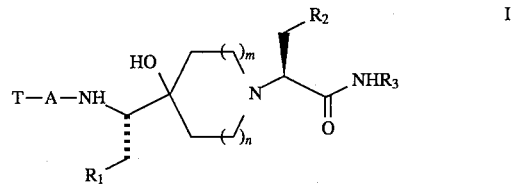

wherein:
m=0,1;
n=0,1;
R$_1$ and R$_2$ are independently
  a) aryl unsubstituted or substituted with one or more of C$_{1-4}$ lower alkyl, hydroxy, C$_{1-3}$ alkoxy or halo;
  b) C$_5$–C$_7$ cycloalkyl; or
  c) heterocycle unsubstituted or substituted with one or more of C$_{1-4}$ lower alkyl, hydroxy, C$_{1-3}$ alkoxy or halo;
R$_3$ is
  a) hydrogen;
  b) C$_{1-6}$ alkyl, unsubstituted or substituted with one or more of hydroxy, C$_{1-3}$ alkoxy, aryl, heterocycle or halo;
  c) aryl unsubstituted or substituted with one or more of C$_{1-4}$ lower alkyl, hydroxy, C$_{1-3}$ alkoxy or halo;

d) heterocycle unsubstituted or substituted with one or more of $C_{1-4}$ lower alkyl, hydroxy, $C_{1-3}$ alkoxy or halo; or e) a 5 to 7 membered carbocyclic or 7–10 membered bicyclic carbocyclic ring, such as cyclopentane, cyclohexane, indan, norbornane, naphthalene, thiopyran, isothiopyran, or benzopyran, the carbocyclic ring being unsubstituted or substituted with one or more of $C_{1-4}$ lower alkyl, hydroxy, $C_{1-3}$ alkoxy or halo; and T is $R_4OC(O)$, $R_4C(O)$ or $R_4NR_5C(O)$ wherein $R_4$ is a) $C_{1-5}$ alkyl unsubstituted or substituted with one or more of aryl, heterocycle, hydroxy, halo or $C_{1-3}$ alkoxy;

b) 5-to 7-membered carbocycle or carbocycle-$C_{1-4}$alkyl wherein the carbocycle is either saturated, partially saturated or unsaturated, any of which carbocycle is unsubstituted or substituted with one or more of $C_{1-4}$ alkyl, $C_{2-4}$ alkenyl, $C_{1-3}$ alkoxy, halo-$C_{1-3}$ alkyl, aryl-$C_{1-3}$ alkyl, or $C_{3-5}$ cycloalkyl;

c) 5- to 7-membered heterocycle or heterocyclic-$C_{1-4}$alkyl wherein the heterocycle has one or two heteroatoms selected from O, N or S, any of which heterocycle is unsubstituted or substituted with one or more of $C_{1-4}$ alkyl, $C_{2-4}$ alkenyl, oxo, $C_{3-5}$ cycloalkyl, or $C_{1-3}$ alkoxy;

d) aryl unsubstituted or substituted with one or more of $C_{1-4}$ lower alkyl, hydroxy, $C_{1-3}$ alkoxy or halo; or e) heterocycle; and $R_5$ is a) hydrogen, or b) $C_{1-4}$ alkyl unsubstituted or substituted with one or more of $C_{2-4}$ alkenyl, $C_{1-3}$ alkoxy, halo-$C_{1-3}$ alkyl, hydroxy-$C_{2-4}$ alkyl, aryl-$C_{1-3}$ alkyl, or $C_{3-5}$ cycloalkyl; and A is absent or a) an L-amino acid chosen from valine, isoleucine, leucine, alanine, asparagine or serine; or b) a 5- to 7-membered heterocycle or heterocycle-$C_{1-4}$alkyl wherein heterocycle has one or two heteroatoms selected from O, N or S, any of which heterocycle is unsubstituted or substituted with one or more of $C_{1-4}$ alkyl, $C_{2-4}$ alkenyl, oxo, $C_{3-5}$ cycloalkyl, or $C_{1-3}$ alkoxy, or pharmaceutically acceptable salt thereof.

The compounds of the present invention may have asymmetric centers and occur as racemates, racemic mixtures and as individual diastereomers or enantiomers, or mixtures thereof, with all isomeric forms being included in the present invention.

When any variable (e.g., heterocycle, $R_1$ or $R_2$, etc.) occurs more than one time in any constituent or in Formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents an alkyl group of indicated number of carbon atoms attached through an oxygen bridge. "Alkenyl" is intended to include a hydrocarbon chain of either a straight or branched configuration and one or more unsaturated carbon-carbon bonds which may occur in any stable point along the chain, such as ethenyl, propenyl, butenyl, pentenyl, and the like. "Halo", as used herein, means fluoro, chloro, bromo or iodo.

As used herein, with exceptions as noted, "aryl" is intended to mean phenyl (Ph) or naphthyl. "Carbocyclic" is intended to mean any stable 5- to 7-membered carbon ring or 7- to 10-membered bicyclic carbon ring, any of which may be saturated or partially unsaturated.

The term heterocycle or heterocyclic, as used herein except where noted, represents a stable 5- to 7-membered mono- or bicyclic or stable 7- to 10-membered bicyclic heterocyclic ting system, any ring of which may be saturated or unsaturated, and which consists of carbon atoms and from one to three heteroatoms selected from the group consisting of N, O and S, and wherein the nitrogen and sulfur heteroatoms may optionally be oxidized, and including any bicyclic group in which any of the above-defined heterocyclic tings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiopyranyl, tetrahydrofuryl, tetrahydropyranyl, and tetrahydrothienyl, thienyl, benzothienyl, thiamorpholinyl, thiamorpholinyl sulfoxide, thiamorpholinyl sulfone and isobenzothiopyranyl.

The pharmaceutically-acceptable salts of the compounds of Formula I (in the form of water- or oil-soluble or dispersible products) include the conventional non-toxic salts or the quaternary ammonium salts of these compounds, which are formed, e.g., from inorganic or organic acids. Examples of such acid addition salts include acetate, adipate, alginate, aspanate, benzoate, bisulfate, citrate, digluconate, dodecylsulfate, fumarate, glycerophosphate, hemisulfate, hydrochloride, 2-hydroxy-ethanesulfonate, factate, maleate, methanesulfonate, succinate and tartrate.

In a preferred embodiment of this invention,

A is absent;

T is $R_4OC(O)$;

$R_1$ and $R_2$ are independently phenyl or cyclohexyl, any of which is unsubstituted or substituted with hydroxy or $C_{1-3}$ alkoxy;

$R_3$ is $C_{1-5}$ alkyl, unsubstituted or substituted with one or more of hydroxy or $R_3$ is 1(S)(2(R)-hydroxyindan);

$R_4$ is a $C_{1-5}$ alkyl or a 5- to 7-membered heterocycle having one heteroatom selected from O or S, any of which heterocycle is unsubstituted or substituted with one or more of $C_{1-4}$ alkyl, $C_{2-4}$ alkenyl, oxo or $C_{1-3}$ alkoxy.

A second embodiment is further limited to compounds wherein:

T is $R_4OC(O)$;

$R_1$ and $R_2$ are phenyl;

$R_3$ is t-butyl, 2-methylpropyl or 1(S)(2(R)-hydroxyindan); and $R_4$ is i) $C_{1-5}$ alkyl; or ii) 1,1-dioxo-tetrahydrothienyl or tetrahydrofuranyl, unsubstituted or substituted with $C_{1-4}$ alkyl, $C_{2-4}$ alkenyl or $C_{1-3}$ alkoxy.

A third embodiment is further limited to compound wherein:

$R_4$ is i) $C_{1-5}$ alkyl; or ii) tetrahydrofuran-3-yl or 1,1-dioxotetrahydrothien-3-yl, unsubstituted or substituted with methyl, ethyl, n-propyl, i-propyl, methoxy, ethoxy, or propenyl.

In a fourth preferred embodiment, $R_1$ and $R_2$ are phenyl;

$R_3$ is 1(S)(2(R)-hydroxyindan); and $R_4$ is a $C_{1-5}$ alkyl or 5- to 7-membered heterocycle having one S heteroatom, said heterocycle unsubstituted or substituted with one or more of $C_{1-4}$ alkyl, oxo or $C_{3-5}$ cycloalkyl.

A fifth embodiment is further limited to:

$R_1$ and $R_2$ are phenyl;

$R_3$ is 1(S)(2(R)-hydroxyindan);

$R_4$ is i) $C_{1-5}$ alkyl; or ii) 1,1-dioxotetrahydrothien-3-yl, unsubstituted or substituted with $C_{1-4}$ alkyl, or $C_{3-5}$ cycloalkyl.

Most preferred compounds of this invention include the following:

Compound A

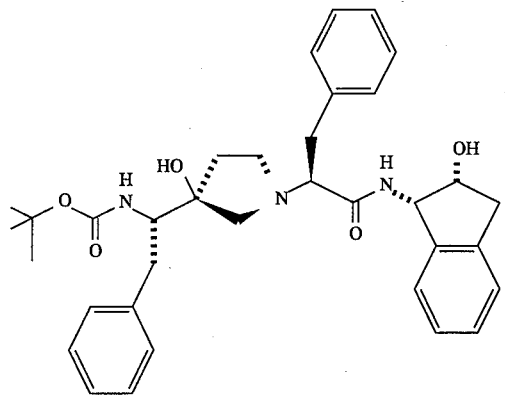

N-(1'(S)-(2'(R)-hydroxyindanyl))-2(S)-(1'-(3'(S)-hydroxy-3'(S)-(1"(S)-ten-butyloxycarbonylamino-2"-phenylethyl)pyrrolidinyl))-3-phenylpropane-amide; or Compound B

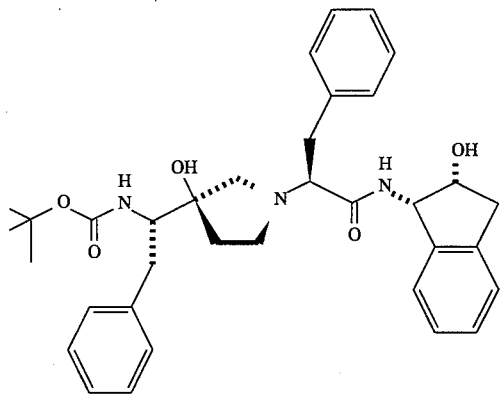

N-(1'(S)-(2'(R)-hydroxyindanyl))-2(S)-(1'-(3'(R)-hydroxy-3'(R)-(1"(S)-tert-butyloxycarbonylamino-2"-phenylethyl)pyrrolidinyl))-3-phenylpropane-amide; or Compound C

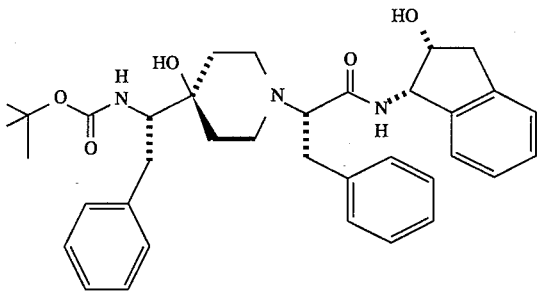

N-(1'(S)-(2'(R)-hydroxyindanyl))-2(S)-(4'(S)-hydroxy-4'(S)-(1"(S)-ten-butyloxycarbonylamino-2"-phenylethyl)piperidinyl)-3-phenylpropane-amide; or Compound D

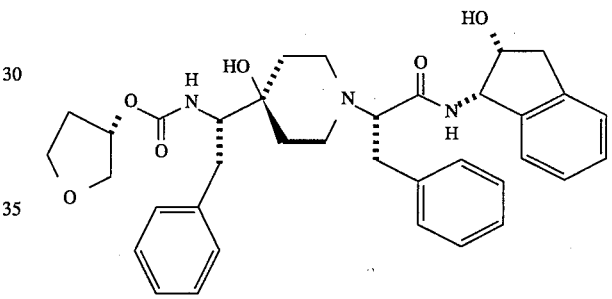

N-(1'(S)-(2'(R)-hydroxyindanyl))-2(S)-(4'-hydroxy-4'-(1"(S)-( 3'"(S)-tetrahydrofuryloxycarbonyl)amino- 2"-phenyl)ethyl-1'-piperidinyl)-3-phenylpropane-amide; or Compound E

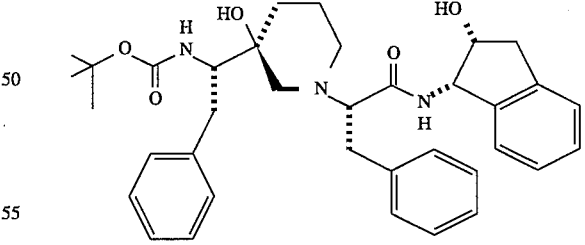

N-(1'(S)-(2'(R)-hydroxyindanyl))-2(S)-(3'(S)-hydroxy-3'(S)-(1"(S)-tert-butyloxycarbonylamino- 2"-phenylethyl)-1'-piperidinyl)-3-phenylpropane-amide; or

Compound F

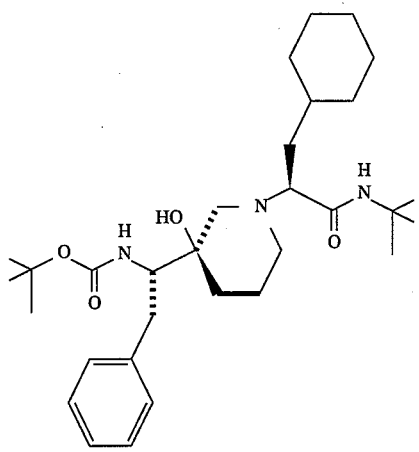

named, N-(1',1'-dimethylethyl)-2(S)-(3'(R)-hydroxy- 3'(R)-(1"(S)-tert-butyloxycarbonylamino- 2"-phenylethyl)-1'-piperidinyl)-3-cyclohexylpropaneamide; or pharmaceutically acceptable salt thereof.

The compounds of the present invention are prepared in accordance with Schemes I–IV.

SCHEME 1

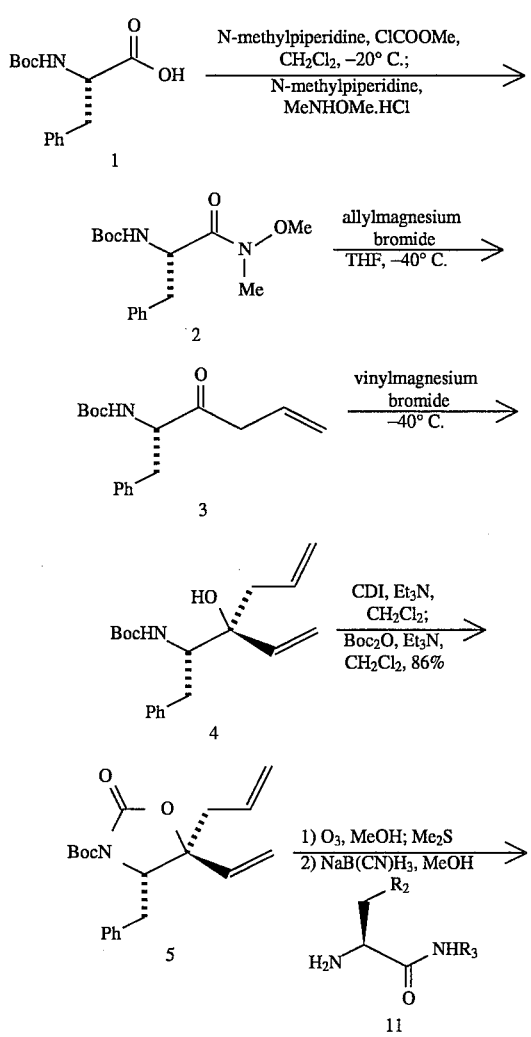

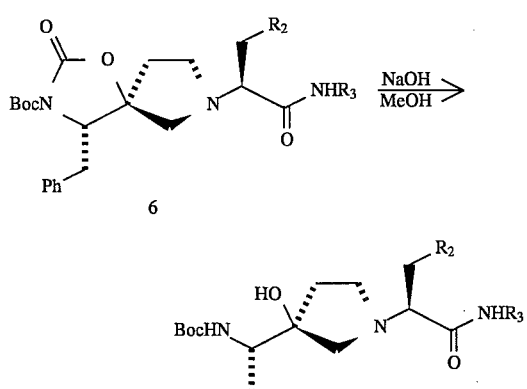

Compound 2 is prepared by coupling of compound 1 with methoxymethylamine under the effect of N-methylpiperidine and methyl chloroformate. Reaction of Compound 2 with allylmagnesium bromide provides compound 3, which is converted to compound 4 by addition of vinylmagnesium bromide. Compound 4 is protected as oxazolidinone 5. Ozonolysis of compound 5 followed by condensation with amine 11 under reductive amination conditions provides compound 6. Hydrolysis of the protecting group in compound 6 gives compound 7. The amine 11 is prepared from the coupling of an amino acid 8 and amine 9 followed by deprotection of the tert-butyloxycarbonyl group of compound 10. Example 1 illustrates but does not limit Scheme 1.

SCHEME 2

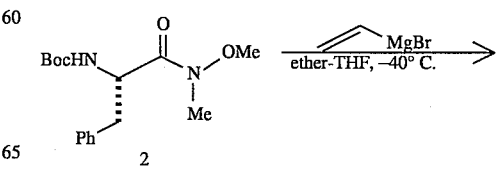

-continued
SCHEME 2

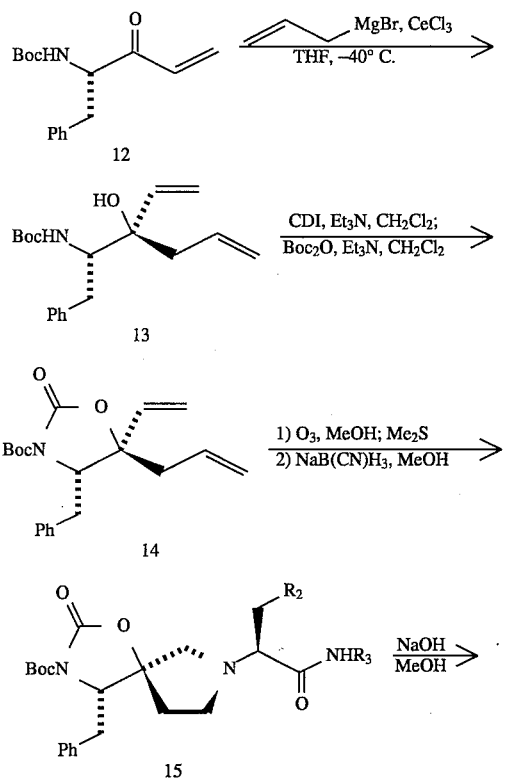

-continued
SCHEME 3

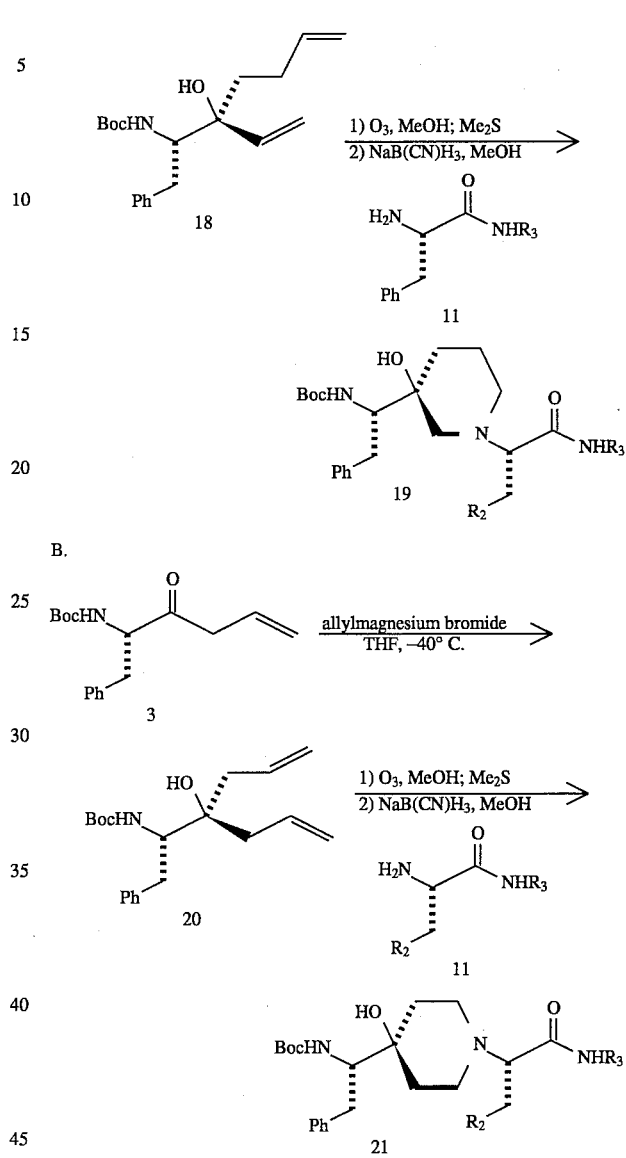

Compound 12 is obtained from the reaction of compound 2 with vinylmagnesium bromide. Addition of allylmagnesium bromide to compound 12 was effected under the influence of $CeCl_3$ to provide compound 13. Compound 16 is then prepared from compound 13 in the same manner as compound 6 was prepared from compound 4. Example 2 illustrates but does not limit Scheme 2.

SCHEME 3

A.

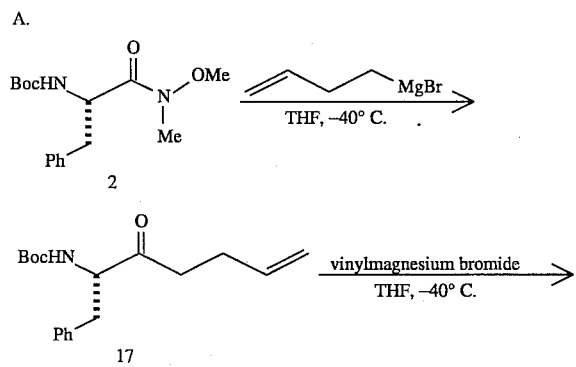

-continued
SCHEME 3

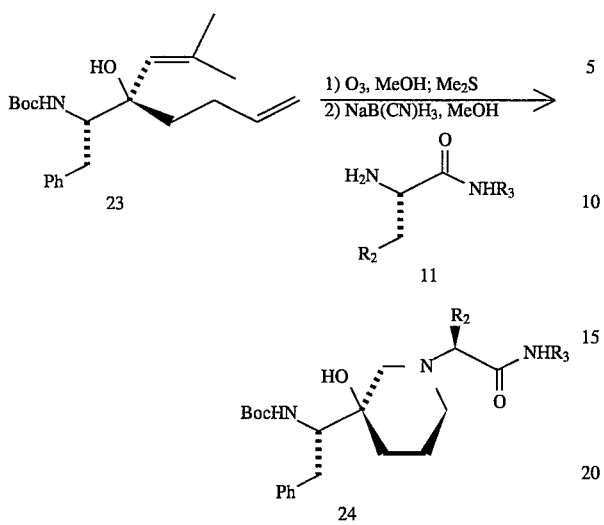

Compound 17 was prepared from compound 2 using 3-butenylmagnesium bromide. Addition of vinylmagnesium bromide to compound 17 provides compound 18. Reaction of compound 3 with allylmagnesium bromide provides compound 20. Reaction of compound 2 with 2-methyl-1-propenylmagnesim bromide provides compound 22 which was convened to compound 23 by addition of 3-butenylmagnesium bromide. From compounds 18, 20, and 23 compounds 19, 21, and 24 are prepared, respectively, according to the same method that was used for the preparation of compound 6 from 5. Examples 3–5 illustrate but does not limit Scheme 3.

SCHEME 4

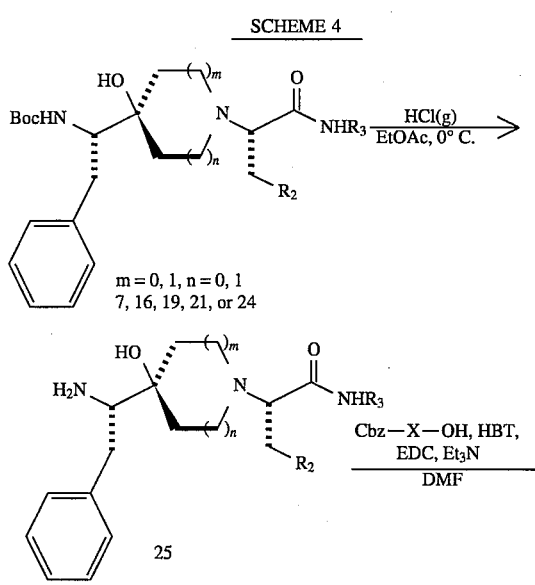

-continued
SCHEME 4

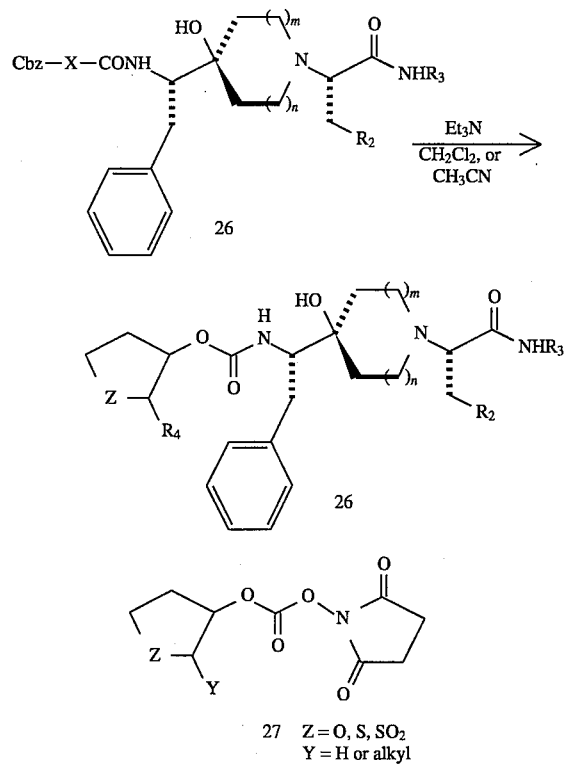

Treatment of compound 7, 16, 19, 21 or 24 with gaseous HCl in cold EtOAC or trifluoroacetic acid in dichloromethane provides the amine 25. Coupling of compound 25 with N-protected amino acid under the effect of HBT, EDC in DMF yields compound 26. Compound 28 is prepared by the reaction of compound 25 with compound 27 in the presence of triethylamine in dichloromethane or acetonitrile.

Other substituents for X, $R_1$, $R_2$, $R_3$ and $R_4$ in Formula I are readily prepared by those skilled in the art, by substituting and/or protecting appropriate groups in the schemes outlined above.

The compounds of the present invention include but are not limited to those of the following Table 1:

TABLE I
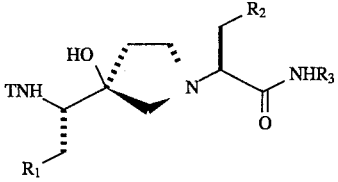
| $R_1$ | $R_2$ | $R_3$ | T |
|---|---|---|---|
| Ph | Ph | 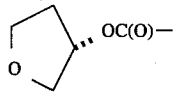 | 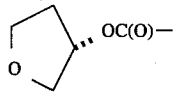 |
| Ph | Ph | 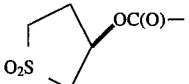 | 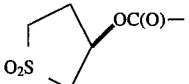 |
| Ph | Ph | 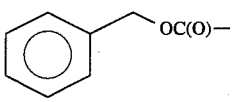 | 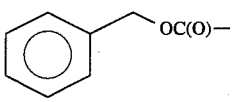 |
| Ph | Ph | 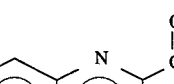 | 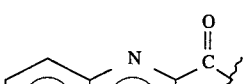 |
| Ph | 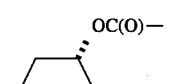 | 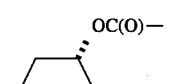 | 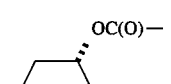 |
| 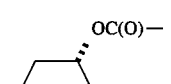 | Ph | 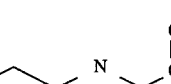 | 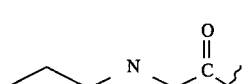 |
| 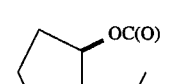 | Ph | 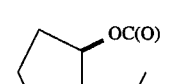 |  |
|  | Ph |  |  |

TABLE I-continued
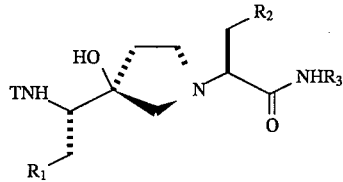
| R₁ | R₂ | R₃ | T |
|---|---|---|---|
| Ph | Ph | 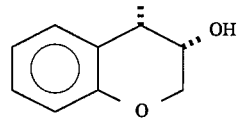 | 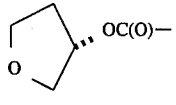 |
| Ph | Ph | 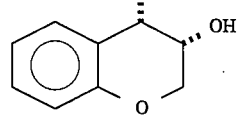 | 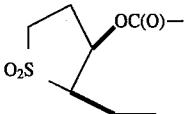 |
| Ph | Ph | 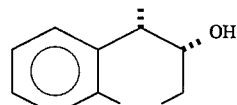 | 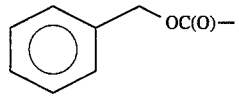 |
| Ph | Ph | 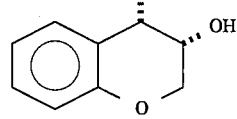 | 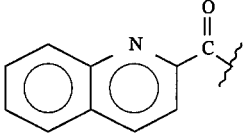 |
| Ph |  | 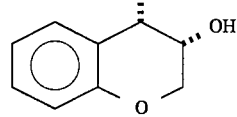 | 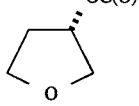 |
|  | Ph | 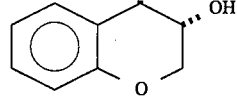 | 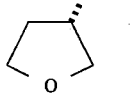 |
|  | Ph | 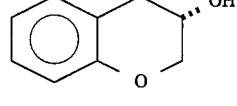 | 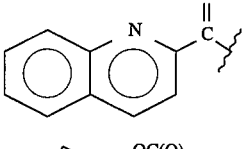 |
|  | Ph | 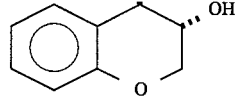 | 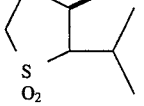 |
| Ph | Ph | 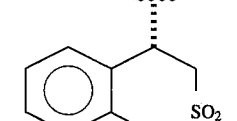 | 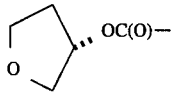 |

TABLE I-continued
| R₁ | R₂ | R₃ | T |
|---|---|---|---|
| Ph | Ph | 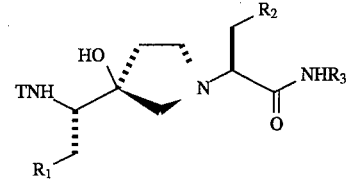 | 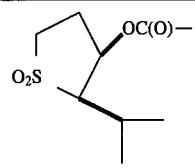 |
| Ph | Ph | 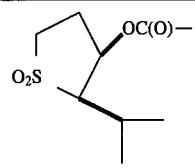 | 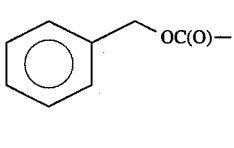 |
| Ph | Ph | 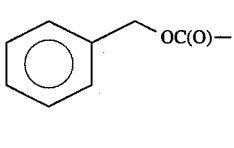 | 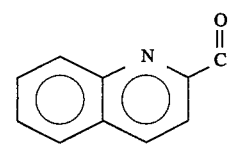 |
| Ph | 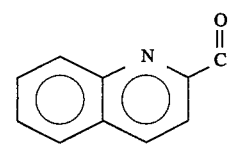 | 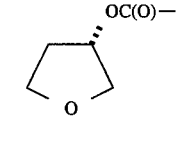 | 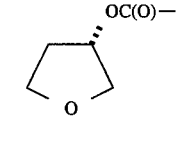 |
| 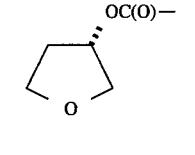 | Ph | 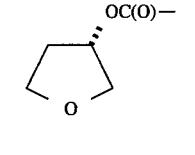 | 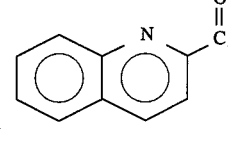 |
| 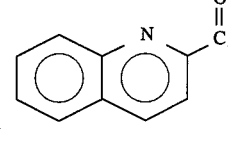 | Ph | 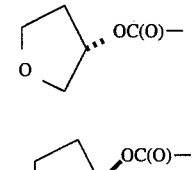 | 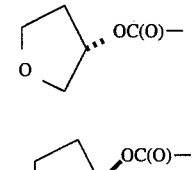 |
| Ph | Ph | 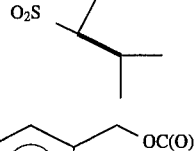 | 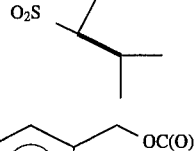 |
| Ph | Ph |  |  |
| Ph | Ph | | |

TABLE I-continued
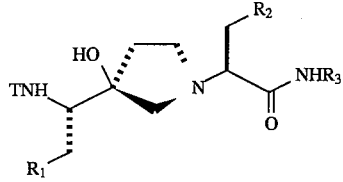
| $R_1$ | $R_2$ | $R_3$ | T |
|---|---|---|---|
| Ph | Ph | 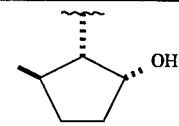 | 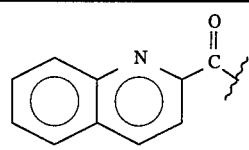 |
| Ph |  | 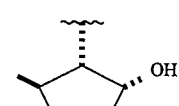 | 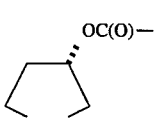 |
| 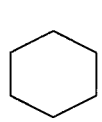 | Ph | 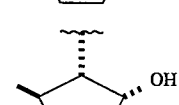 | 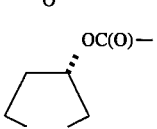 |
| 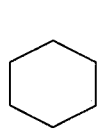 | Ph | 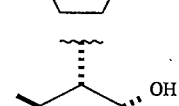 | 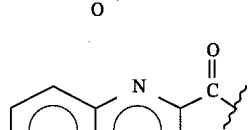 |
| 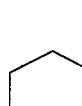 | Ph | 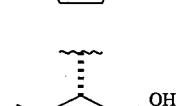 | 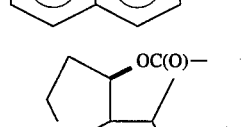 |
TABLE II
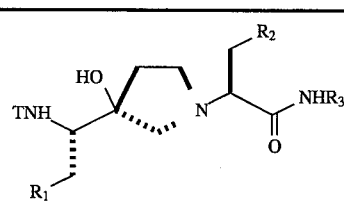
| $R_1$ | $R_2$ | $R_3$ | T |
|---|---|---|---|
| Ph | Ph | 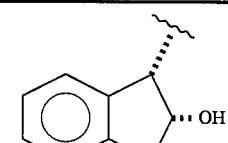 | 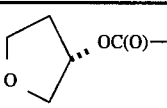 |
| Ph | Ph | 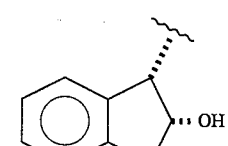 | 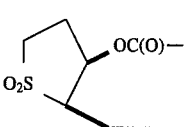 |

TABLE II-continued

| R₁ | R₂ | R₃ | T |
|---|---|---|---|
| Ph | Ph | (1S,2R)-1-amino-2-hydroxyindanyl | PhCH₂-OC(O)- |
| Ph | Ph | (1S,2R)-1-amino-2-hydroxyindanyl | quinoline-2-C(O)- |
| Ph | Cyclohexyl | (1S,2R)-1-amino-2-hydroxyindanyl | (tetrahydrofuran-3-yl)-OC(O)- |
| Cyclohexyl | Ph | (1S,2R)-1-amino-2-hydroxyindanyl | (tetrahydrofuran-3-yl)-OC(O)- |
| Cyclohexyl | Ph | (1S,2R)-1-amino-2-hydroxyindanyl | quinoline-2-C(O)- |
| Cyclohexyl | Ph | (1S,2R)-1-amino-2-hydroxyindanyl | (2-isopropyl-tetrahydrothiophene-1,1-dioxide-3-yl)-OC(O)- |
| Ph | Ph | (3-hydroxy-chroman-4-yl) | (tetrahydrofuran-3-yl)-OC(O)- |
| Ph | Ph | (3-hydroxy-chroman-4-yl) | (2-isopropyl-tetrahydrothiophene-1,1-dioxide-3-yl)-OC(O)- |

TABLE II-continued

| R₁ | R₂ | R₃ | T |
|---|---|---|---|
| Ph | Ph | 3-hydroxychroman-4-yl | benzyloxycarbonyl |
| Ph | Ph | 3-hydroxychroman-4-yl | quinoline-2-carbonyl |
| Ph | cyclohexyl | 3-hydroxychroman-4-yl | (tetrahydrofuran-3-yl)oxycarbonyl |
| cyclohexyl | Ph | 3-hydroxychroman-4-yl | (tetrahydrofuran-3-yl)oxycarbonyl |
| cyclohexyl | Ph | 3-hydroxychroman-4-yl | quinoline-2-carbonyl |
| cyclohexyl | Ph | 3-hydroxychroman-4-yl | 2-isopropyl-3-(methylsulfonyl)propyl... oxycarbonyl |
| Ph | Ph | 2-hydroxy-5-methylcyclopentyl | (tetrahydrofuran-3-yl)oxycarbonyl |
| Ph | Ph | 2-hydroxy-5-methylcyclopentyl | 2-isopropyl-3-(methylsulfonyl)propyl... oxycarbonyl |
| Ph | Ph | 2-hydroxy-5-methylcyclopentyl | benzyloxycarbonyl |

TABLE II-continued

| R₁ | R₂ | R₃ | T |
|---|---|---|---|
| Ph | Ph | cyclopentyl-OH | quinoline-2-C(O)— |
| Ph | cyclohexyl | cyclopentyl-OH | (tetrahydrofuran-3-yl)-OC(O)— |
| cyclohexyl | Ph | cyclopentyl-OH | (tetrahydrofuran-3-yl)-OC(O)— |
| cyclohexyl | Ph | cyclopentyl-OH | quinoline-2-C(O)— |
| cyclohexyl | Ph | cyclopentyl-OH | isopropyl-CH(SO₂)-CH-OC(O)— |
| Ph | Ph | indane-SO₂ | (tetrahydrofuran-3-yl)-OC(O)— |
| Ph | Ph | indane-SO₂ | isopropyl-CH(SO₂)-CH-OC(O)— |
| Ph | Ph | indane-SO₂ | benzyl-OC(O)— |
| Ph | Ph | indane-SO₂ | quinoline-2-C(O)— |

TABLE II-continued

[Chemical structure diagram showing compound with TNH, HO, R₁, R₂, NHR₃ substituents on a pyrrolidine core]

| R₁ | R₂ | R₃ | T |
|----|----|----|---|
| Ph | [cyclohexyl] | [benzyl-SO₂ substituted] | [tetrahydrofuranyl-OC(O)–] |
| [cyclohexyl] | Ph | [benzyl-SO₂ substituted] | [tetrahydrofuranyl-OC(O)–] |
| [cyclohexyl] | Ph | [benzyl-SO₂ substituted] | [quinolinyl-C(O)–] |
| [cyclohexyl] | Ph | [benzyl-SO₂ substituted] | [O₂S-CH(OC(O)–)-CH(CH₃)-] |

The compounds of the present invention are useful in the inhibition of HIV protease, the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymtomatic, and actual or potential exposure to HIV. For example, the compounds of this invention are useful in treating infection by HIV after suspected past exposure to HIV by e.g., blood transfusion, accidental needle stick, or exposure to patient blood during surgery.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be sold for these purposes.

For these purposes, the compounds of the present invention may be administered orally, parenterally (including subcutaneous injections, intravenous, intramuscular, intrastemal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention, or a pharmaceutically-acceptable salt thereof.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, flourocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Dosage levels of the order of 0.02 to 5.0 or 10.0 grams-per-day are useful in the treatment or prevention of the above-indicated conditions, with oral doses two-to-five times higher. For example, infection by HIV is effectively treated by the administration of from 1.0 to 50 milligrams of the compound per kilogram of body weight from one to three times per day. It will be understood, however, that the specific dose level and frequency of dosage for any particular patient may be varied and will depend upon a variety of factors including the activity of the specific compound employed, the metabolic stability and length of action of that compound, the age of the patient, body weight, general health, sex, diet, mode and time of administration, rate of excretion, drug combination, the severity of the particular condition, and the host undergoing therapy.

The present invention is also directed to combinations of the HIV protease-inhibitory compounds with one or more agents useful in the treatment of AIDS.

TABLE C

| Drug Name | Manufacturer | Indication |
|---|---|---|
| ANTIVIRALS | | |
| AL-721 | Ethigen (Los Angeles, CA) | ARC, PGL HIV positive, AIDS |
| Recombinant Human Interferon Beta | Triton Biosciences (Almeda, CA) | AIDS, Kaposi's sarcoma, ARC |
| Acemannan | Carrington Labs (Irving, TX) | ARC (See also immuno-modulators) |
| Cytovene Ganciclovir | Syntex (Palo Alto, CA) | sight threatening CMV peripheral CMV retinitis |
| d4T Didehydrodeoxy-thymidine | Bristol-Myers (New York, NY) | AIDS, ARC |
| ddI Dideoxyinosine | Bristol-Myers (New York, NY) | AIDS, ARC |
| EL10 | Elan Corp, PLC (Gainesville, GA) | HIV infection (See also immuno-modulators) |
| Trisodium Phosphonoformate | Astra Pharm. Products, Inc (Westborough, MA) | CMV retinitis, HIV infection, other CMV infections |
| Dideoxycytidine; ddC | Hoffman-La Roche (Nutley, NJ) | AIDS, ARC |
| Novapren | Novaferon Labs, Inc. (Akron, OH) Diapren, Inc. (Roseville, MN, marketer) | HIV inhibitor |
| Peptide T Octapeptide Sequence | Peninsula Labs (Belmont, CA) | AIDS |
| Zidovudine; AZT AIDS, adv, ARC | Burroughs Wellcome (Rsch. Triangle Park, NC) | AIDS, adv, ARC pediatric AIDS, Kaposi's sarcoma, asymptomatic HIV infection, less severe HIV disease, neurological involvement, in combination with other therapies. |
| Ansamycin LM 427 | Adria Laboratories (Dublin, OH) Erbamont (Stamford, CT) | ARC |
| Dextran Sulfate | Ueno Fine Chem. Ind. Ltd. (Osaka, Japan) | AIDS, ARC, HIV positive asymptomatic |
| Virazole Ribavirin | Viratek/ICN (Costa Mesa, CA) | asymptomatic HIV positive, LAS, ARC |
| Alpha Interferon | Burroughs Wellcome (Rsch. Triangle Park, NC) | Kaposi's sarcoma, HIV in combination w/Retrovir |
| Acyclovir | Burroughs Wellcome | AIDS, ARC, asymptomatic HIV positive, in combination with AZT. |
| Antibody which neutralizes pH labile alpha aberrant Interferon in an immuno-adsorption column | Advanced Biotherapy Concepts (Rockville, MD) | AIDS, ARC |
| 661 | Merck (Rahway, NJ) | AIDS, ARC, asymptomatic HIV positive, also in combination with AZT. |
| 229 | Merck (Rahway, NJ) | AIDS, ARC, asymptomatic HIV positive, also in combination with AZT. |
| Nevirapine | Boehringer Ingelheim | AIDS, ARC, asymptomatic HIV positive, also in combination with AZT. |
| IMMUNO-MODULATORS | | |
| AS-101 | Wyeth-Ayerst Labs. (Philadelphia, PA) | AIDS |
| Bropirimine | Upjohn (Kalamazoo, MI) | advanced AIDS |
| Acemannan | Carrington Labs, Inc. (Irving, TX) | AIDS, ARC (See also antivirals) |
| CL246,738 | American Cyanamid (Pearl River, NY) Lederle Labs (Wayne, NJ) | AIDS, Kaposi's sarcoma |
| EL10 | Elan Corp, PLC (Gainesville, GA) | HIV infection (See also antivirals) |
| Gamma Interferon | Genentech (S. San Francisco, CA) | ARC, in combination w/TNF (tumor necrosis factor) |
| Granulocyte Macrophage Colony Stimulating Factor | Genetics Institute (Cambridge, MA) Sandoz (East Hanover, NJ) | AIDS |

TABLE C-continued

| Drug Name | Manufacturer | Indication |
|---|---|---|
| Granulocyte Macrophage Colony Stimulating Factor | Hoeschst-Roussel (Sommerville, NJ) Immunex (Seattle, WA) | AIDS |
| Granulocyte Macrophage Colony Stimulating Factor | Schering-Plough (Madison, NJ) | AIDS AIDS, in combination w/AZT seropositive |
| HIV Core Particle Immunostimulant | Rorer (Ft. Washington, PA) | HIV |
| IL-2 Interleukin-2 | Cetus (Emeryville, CA) | AIDS, in combination w/AZT |
| IL-2 Interleukin-2 | Hoffman-La Roche (Nutley, NJ) Immunex | AIDS, ARC, HIV, in combination w/AZT |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute (Miami, FL) | AIDS, ARC |
| Alpha-2 Interferon | Schering Plough (Madison, NJ) | Kaposi's sarcoma w/AZT: AIDS |
| Methionine-Enkephalin | TNI Pharmaceutical (Chicago, IL) | AIDS, ARC |
| MTP-PE Muramyl-Tripeptide | Ciba-Geigy Corp. (Summit, NJ) | Kaposi's sarcoma |
| Granulocyte Colony Stimulating Factor | Amgen (Thousand Oaks, CA) | AIDS, in combination w/AZT |
| rCD4 Recombinant Soluble Human CD4 | Genentech (S. San Francisco, CA) | AIDS, ARC |
| rCD4-IgG hybrids | | AIDS, ARC |
| Recombinant Soluble Human CD4 | Biogen (Cambridge, MA) | AIDS, ARC |
| Interferon Alfa 2A | Hoffman-La Roche (Nutley, NJ) | Kaposi's sarcoma AIDS, ARC, in combination w/AZT |
| SK&F106528 Soluble T4 | Smith, Kline & French Laboratories (Philadelphia, PA) | HIV infection |
| Thymopentin | Immunobiology Research Institute (Annandale, NJ) | HIV infection |
| Tumor Necrosis Factor; TNF | Genentech (S. San Francisco, CA) | ARC, in combination w/gamma Interferon |
| ANTI-INFECTIVES | | |
| Clindamycin with Primaquine | Upjohn (Kalamazoo, MI) | PCP |
| Fluconazole | Pfizer (New York, NJ) | cryptococcal meningitis, candidiasis prevention of oral candidiasis |
| Pastille Nystatin Pastille | Squibb Corp. (Princeton, NJ) | |
| Ornidyl Eflornithine | Merrell Dow (Cincinnati, OH) | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome (Rsch. Triangle Park, NC) | PCP treatment |
| Pentamidine isethionate for inhalation | Fisons Corporation (Bedford, MA) | PCP prophylaxis |
| Spiramycin | Rhone-Poulenc Pharmaceuticals (Princeton, NJ) | cryptosporidial diarrhea |
| Intraconazole-R51211 | Janssen Pharm. (Piscataway, NJ) | histoplasmosis; cryptococcal meningitis |
| Trimetrexate | Warner-Lambert | PCP |
| OTHER | | |
| Recombinant Human Erythropoietin | Ortho Pharm. Corp. (Raritan, NJ) | severe anemia assoc. with AZT therapy |
| Megestrol Acetate | Bristol-Myers (New York, NY) | treatment of anorexia assoc. w/AIDS |
| Total Enteral Nutrition | Norwich Eaton Pharmaceuticals (Norwich, NY) | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Certain compounds of Table C are the following: 661 is 3-([ 4,7-dichloro-1,3-benzoxazol-2-yl )methyl]-amino)-5-ethyl-6-methyl-pyridin- 2(1H)-one; 229 is 3-[2-(1,3-benzoxazol- 2-yl)-ethyl]-5-ethyl-6-methyl-pyridin-2(1H)-one. The synthesis of 661 and 229 is described in EPO 48407 1, and EPO 462800, both herein incorporated by reference. The synthesis of ddC, ddI and AZT are also described in EPO 484071.

Preferred combinations are simultaneous or alternating treatments of an inhibitor of HIV protease and a non-nucleoside inhibitor of HIV reverse transcriptase. An optional third component in the combination is a nucleoside inhibitor of HIV reverse transcriptase, such as AZT, ddC or ddI. A preferred inhibitor of HIV protease is Compound A. Preferred non-nucleoside inhibitors of HIV reverse transcriptase include Compound B, Compound C or nevirapine. These combinations may have synergistic effects on limiting the spread of HIV. Preferred combinations include the following (1) Compound A, with a preferred non-nucleoside inhibitor of HIV reverse transcriptase, and, optionally, AZT or ddI or ddC; (2) Compound A, and any of AZT or ddI or ddC.

ASSAY FOR INHIBITION OF MICROBIAL EXPRESSED HIV PROTEASE

Inhibition studies of the reaction of the protease expressed in Eschericia coli with a peptide substrate [Val-Ser-Gln-Asn-(betanapthyl)Ala-Pro-Ile-Val, 0.5 mg/mL at the time the reaction is initiated] were in 50 mM Na acetate, pH 5.5, at 30° C. for 1 hour. Various concentrations of inhibitor in 1.0 ml DMSO were added to 25 ml of the peptide solution in water. The reaction is initiated by the addition of 15 ml of 0.33 nM protease (0.11 ng) in a solution of 0.133 M Na acetate pH 5.5 and 0.1% bovine serum albumin. The reaction was quenched with 160 ml of 5% phosphoric acid. Products of the reaction were separated by HPLC (VYDAC wide pore 5 cm C-18 reverse phase, acetonitrile gradient, 0.1% phosphoric acid). The extent of inhibition of the reaction was determined from the peak heights of the products. HPLC of the products, independently synthesized, proved quantitation standards and confirmation of the product composition. Compounds A-H showed $IC_{50}$ values ranging 200→3,000 nM.

CELL SPREAD ASSAY

Inhibition of the spread of HIV in cell culture was measured according to Nunberg, J. H. et al., *J. Virol.* 65, 4887 (1991). In this assay, MT-4 T-lymphoid cells were infected with HIV-1 (wild-type, unless otherwise indicated) by using a predetermined inoculum, and cultures were incubated for 24 h. At this time, ≦1% of the cells were positive by indirect immunofluorescence. Cells were then extensively washed and distributed into 96-well culture dishes. Serial twofold dilutions of inhibitor were added to the wells, and cultures were continued for 3 additional days. At 4 days postinfection, 100% of the cells in control cultures were infected. HIV-1 p24 accumulation was directly correlated with virus spread. The cell culture inhibitory concentration was defined as the inhibitor concentration in nanomoles/liter which reduced the spread of infection by at least 95%, or $CIC_{95}$.

INHIBITION OF VIRUS SPREAD

A. Preparation of HIV-infected MT-4 cell Suspension

MT cells were infected at Day 0 at a concentration of 250,000 per ml with a 1:1000 dilution of HIV-1 strain IIIb stock (final 125 pg p24/ml; sufficient to yield ≦1% infected cells on day 1 and 25–100% on day 4). Cells were infected and grown in the following medium: RPMI 1640 (Whittaker BioProducts), 10% inactivated fetal bovine serum, 4 mM glutamine (Gibco Labs) and 1:100 Penicillin-Streptomycin (Gibco Labs).

The mixture was incubated overnight at 37° C. in 5% $CO_2$ atmosphere.

B. Treatment with Inhibitors

A matrix of nanomolar range concentrations of the pairwise combinations is prepared. At Day 1, aliquots of 125 ml of inhibitors are added to equal volumes of HIV-infected MT-4 cells (50,000 per well) in a 96-well microtiter cell culture plate. Incubation is continued for 3 days at 37° C. in 5% $CO_2$ atmosphere.

C. Measurement of Virus Spread

Using a multichannel pipettor, the settled cells are resuspended and 125 ml harvested into a separate microtiter plate. The supernatant is assayed for HIV p24 antigen.

The concentration of HIV p24 antigen is measured by an enzyme immunoassay, described as follows. Aliquots of p24 antigen to be measured are added to microwells coated with a monoclonal antibody specific for HIV core antigen. The microwells are washed at this point, and at other appropriate steps that follow. Biotinylated HIV-specific antibody is then added, followed by conjugated streptavidin-horseradish peroxidase. A color reaction occurs from the added hydrogen peroxide and the concentration of HIV p24 antigen.

Calculation of Degree of Synergy

When there is synergy pairwise combinations of inhibitors are found to exhibit markedly enhanced inhibition of virus spread, in comparison to each inhibitor alone, or in comparison to merely additive inhibition of each inhibitor.

The data is processed as follows: fractional inhibitory concentration ratios (FIC) are calculated according to Elion, et al., *J. Biol. Chem.*, 208, 477 (1954). The minimum sum of FICS, which is the maximum synergy, is determined for various pairwise combinations. The smaller the number, the greater the synergy.

EXAMPLE 1

Step 1

Preparation of N',N'-methoxymethyl-N-tert-butyloxycarbonylphenylalanine-carboxamide, compound 2

N,O-dimethylhydroxylamine hydrochloride (3.102 g, 31.8 mmol) in 20 mL dichloromethane was placed in a 100 mL 3-neck flask equipped with a magnetic stirrer, digital thermometer, nitrogen inlet tube and a dropping funnel. The suspension was stirred at 0° C. and N-methylpiperidine (3.92 mL, 32.3 mmol) was added dropwise to maintain the internal temperature at 2°±2° C. A clear colorless solution resulted. In a 1 L 3-neck flask equipped with a magnetic stirrer, nitrogen inlet tube, dropping funnel and digital thermometer was placed 7.96 g (30.0 mmol) of L-phenylalanine in 35 mL of dry THF and 120 mL of dry dichloromethane. The solution was stirred at –20° C. and N-methylpiperidine (3.92 mL, 32.3 mmol) was added rapidly via dropping funnel. Temperature rose to 5° C. Methylchloroformate (2.48 mL, 32.1 mmol) was added rapidly keeping the reaction temperature at –15° C. After 5 min, previously prepared N,O-dimethylhydroxylamine solution was added keeping the reaction temperature at –12°±1° C. After completing the addition, the cooling bath was removed and the clear reaction mixture was warmed to room temperature and stirring was continued overnight (15 h). The reaction mixture was cooled to 0° C., washed with 2×40 mL 10% citric acid solution. The organic phase was cooled to 0° C. and washed with 2×40 mL of NaOH solution and 40 mL of brine. It was dried over anhyd $MgSO_4$ and filtered and concentrated under reduced pressure (bath temperature<30° C.). When the residue was dried under high vacuum, 8.791 g of colorless oil was obtained (95% yield). $^1H$ NMR ($CDCl_3$) 1.39 (9H, s), 2.88 (1H, ABX, $J_{AB}$=13.0 Hz, $J_{AX}$=7.6 Hz), 3.05 (1H, $J_{AB}$=13.2 Hz, $J_{BX}$=6.4 Hz), 3.17 (3H, s), 3.66 (3H, s), 4.96 (1H, m), 5.28 (1H, d, 7.6 Hz), 7.24–7.42 (5H, m).

Step 2

Preparation of (2S)-N-(1,1-dimethylethoxy-carbonylamino)-1-phenyl-5-hexen-3-one compound 3

To a magnetically stirred solution of allylmagnesium bromide in ether (1.0 M solution, 12.97 mL, 12.97 mmol) was added 15 mL of dry THF. The mixture was cooled to –78° C. and N',N'methoxymethyl-N-tert-butyloxycarbonylphenylalanine-carboxamide in THF (10 mL) was added dropwise over a period of 10 min. Stirring was continued for ~1 h and the flask was allowed to warm up to room temperature. When there was no starting material by TLC, 10% citric acid solution (20 mL) was added to the mixture and it was extracted with ethyl ether (20 mL×3) and the ether extracts were combined. The combined organic solution was washed with sat aq $NaHCO_3$ solution (20 mL), water (20 mL), and brine (20 mL), and dried over anhyd $MgSO_4$. Filtered solution was concentrated to give 1.49 g (99% yield) of a colorless residue. $^1H$ NMR ($CDCl_3$) 7.15–7.35

(5H, m), 5.83–5.92 (1 H, m), 5.05–5.21 (3H, m), 4.59 (1H, m), 2.95–3.26 (4H, m), 1.41 (9H, s).

Step 3

Preparation of
(2S)-N-(1,1-dimethylethoxy-carbonylamino)-
3-ethenyl-3(S)-hydroxy-1-phenyl-5-hexene,
compound 4

To a magnetically stirred solution of vinylmagnesium bromide in ether (1.0 M, 10.4 mL) at –40° C. was added a THF solution (5 mL) of (2S)-N-(1,1-dimethylethoxy-carbonylamino)-1-phenyl- 5-hexen-3-one (0.752 g, 2.60 mmol) over a period of 5 min. The mixture was stirred for 1 h at –40≠–30° C. and then slowly warmed up to room temperature over a period of 2 h. After addition of 10% aq citric acid solution (10 mL), the mixture was diluted with ether (10 mL) and layers separated. The aq layer was extracted with ether (2×5 mL) the organic layers combined. Combined organic layers were washed with sat aq NaHCO$_3$ solution (10 mL) and brine (15 mL). Drying (over anhyd MgSO$_4$) followed by concentration provided a crude product, which was purified on a silica gel chromatographic column to provide 0.396 g (50%) of desired product. $^1$H NMR (CDCl$_3$) 7.15– 7.32 (5H, m), 5.95 (1H, dd, J=12, 17 Hz), 5.84 (1H, m), 5.37 (1H, d, J=18 Hz), 5.16–5.28 (3H, m), 4.46 (1H, d, J=7.6 Hz), 3.82 (1H, m), 3.18 (1H, ABX, J$_{AB}$=14.0, J$_{AX}$=5.1 Hz), 2.69 (1H, ABX, J$_{AB}$=14.1, J$_{BX}$=12Hz), 2.48 (2H, d, J=7.0 Hz), 1.95 (1H, br s), 1.27 (9H, s).

Step 4

Preparation of
(4S)-phenylmethyl-3-N-(1,1-dimethylethoxy-carbonyl)-
5(S)-ethenyl-5(S)-(2'-propenyl)oxazolidin- 2-one,
compound 5

To a magnetically stirred solution of (2S)-N-(1,1-dimethylethoxy-carbonylamino)- 3-ethenyl-3(S)-hydroxy-1-phenyl-5-hexene (0.833 g, 2.00 mmol) in 10 mL THF was added NaH (60% dispersion in mineral oil, 0.314 g, 7.86 mmol) and stirring was continued for 0.5 h. Carbonyldiimidazole (0.637 g, 3.93 mmol) and Boc-anhydride (1.144 g, 5.24 mmol) were added and the mixture was stirred for 4 h. Sat aq NH$_4$Cl solution (10 mL) was added to the reaction mixture and it was extracted with EtOAC (15 mL×3). The combined organic layers were dried over anhyd Na$_2$SO$_4$, filtered and concentrated under reduced pressure. Silica gel column chromatography (10% EtOAc in hexane) furnished a white solid (0.738 g, 82% yield). mp 104°–105.5° C.; $^1$H NMR (CDCl$_3$) 7.25–7.38 (5H, m), 5.70 (1H, dd, I=10.9, 17.2 Hz), 5.66 (1H, m), 5.12–5.40 (3H, m), 5.11 (1H, dd, J=1.2, 16.9 Hz), 4.40 (1H, dr, J=6.9, 7.2 Hz), 3.08 (1H, dd, J=3.0, 6.7 Hz), 2.73 (1H, ABX, J$_{AB}$=14.5 Hz, J$_{AX}$=6.5 Hz), 2.32 (1H, ABX, J$_{AB}$=14.5 Hz, J$_{BX}$=7.7 Hz), 1.38 (9H, s).

Step 5

Preparation of
N-(1'(S)-(2'(R)-hydroxyindanyl)-2(S)-amino-
3-phenylpropanamide compound 11

To a magnetically stirred solution of N-tert-butyloxycarbonylphenylalanine (2.653 g, 10.0 mmol) in DMF (25 mL) were added 1(S)-amino-2(R)-hydroxyindan (1.79 g, 12.0 mmol), HBT (1.486 g, 11.0 mmol) and EDC (2.109 g, 11.0 mmol). Triethylamine was added to adjust the pH of the mixture to –8.5. Stirring was continued for 15 h. DMF was removed in vacuo and the residue was partitioned between 10% aq citric acid solution (20 mL) and EtOAC (20 mL). The organic layer was washed with 10% aq citric acid solution (20 mL), sat aq NaHCO$_3$ solution (20 mL), and brine (20 mL) and dried over anhyd MgSO$_4$. The solution was filtered and concentrated to give a white solid. The crude product was recrystalized in 75% EtOAc in hexane to furnish 3.64 g (92% yield) of N-(1(S)-(2(R)-hydroxyindanyl)- 2(S)-(tert-butyloxycarbonyl)amino-3-phenylpropanamide (compound 10) as a white flake. mp 147.5–148.5° C.; $^1$H NMR (CDCl$_3$) 7.20–7.40 (9H, m), 6.22 (1H, d, J=7.6 Hz), 5.36 (1H, rid, J=5.7, 7.6 Hz), 5.22 (1H, m), 4.44 (1H, m), 4.38 (1H, m), 3.22 (1H, dd, J=7.0, 12.7 Hz), 3.10 (1H, m), 3.07 (1H, m), 2.86 (1H, dd, J=12.7, 1.6 Hz), 1.41 (9H, s).

To a magnetically stirred solution of compound 10 (1.503 g, 3.79 mmol) in EtOAc (250 mL) at 0° C. was bubbled in dry HCl gas for 30 min. Stirring was continued for 0.5 h at 0° C. Solvent was removed under reduced pressure and the residue dissolved in dichloromethane (50 mL). The solution was washed with sat aq NaHCO$_3$ solution (30 mL) and brine (30 mL), dried over anhyd Na$_2$SO$_4$, filtered and concentrated under reduced pressure. The crude product was recrystallized from MeOH/EtOAc/hexene to provide 0.947 g (84% yield) of a colorless needle. mp 180°–181° C.; $^1$H NMR (CDCl$_3$) 7.66 (1H, d, J=7.8 Hz), 7.15–7.38 (9H, m), 5.27 (1H, dd, J=4.9, 7.6 Hz), 4.52 (1H, br s), 3.84 (1H, dd, J=6.6, 7.0 Hz), 3.23 (1H, dd, J=5.9, 13.7 Hz), 3.11 (1 H, dd, J=4.8, 16.0 Hz), 3.03 (1 H, dd, J=8.3, 13.8 Hz), 2.90 (1H, d, J:16.7 Hz).

Step 6

Preparation of
N-(1'(S)-(2'(R)-hydroxyindanyl))-2(S)-(1'-
(3'(S)-hydroxy-3'-(1''(S)-tert-butyloxycarbonylamino-
2''-phenylethyl)pyrrolidinyl))-3-phenylpropane-amide,
compound 7

(4S)-Phenylmethyl-3-N-(1,1-dimethylethoxy-carbonyl)-5(S)-ethenyl-5(S)-(2'-propenyl)oxazolidin-2-one (0.060 g, 0.175 mmol) in 4 mL, methanol was cooled to –78° C. and ozone was bubbled into the solution until it turned to blue. Dimethyl sulfide (≠0.1 mL) was added at –78° C. and the mixture was allowed to warm to room temperature. Solvent was removed under reduced pressure. The residue was dissolved in methanol (3 mL) and N-(1(S)-(2(R)-hydroxyindanyl)- 2(S)-amino-3-phenylpropanamide (0.062 g, 0.210 mmol) and 4Å molecular sieves were added. After stirring for 0.5 h, NaCNBH$_3$ (0.053 g, 0.838 mmol) and two drops of acetic acid were added. Stirring was continued for 24 h. The reaction mixture was then partitioned between sat aq Na$_2$CO$_3$ solution (10 mL) and EtOAc (10 mL) and the aqueous layer was extracted with EtOAc (5 mL×2). Combined organic layers were so dried over anhyd Na$_2$SO$_4$, filtered and concentrated under reduced pressure. The crude product was purified on a silica gel column chromatography (60% to 80% EtOAc in hexane) to provide 29 mg (27% yield) of compound 6 as a colorless residue.

To a magnetically stirred solution of compound 6 (0.066 g, 0.108 mmol) in 2 mL methanol was added 0.54 mL of 1 N NaOH solution. Stirring was continued for 3 h at room temperature. Solvent was removed under reduced pressure and the residue was dissolved in EtOAc (5 mL) and washed with brine (5 mL). The organic layer was dried over anhyd Na$_2$SO$_4$, filtered and concentrated. The crude product was purified on a preparative TLC (75% EtOAc in hexane) to give 30 mg (47 % yield) of the product as a colorless residue. mp 170° C. (dec); $^1$H NMR (CDCl$_3$) 7.12–7.38 (14H, m), 7.02 (1H, d, J=7.6 Hz), 5.28 (1H, dd, J=10.5, 6.4 Hz), 5.22 (1H, m), 4.32 (1H, m), 3.80 (2H, m), 3.52 (1H, m), 2.82–3.28 (10H, m), 2.42 (1H, m), 1.99 (2H, m), 1.27 (9H, s); MS (M+1)=586; HRMS (M+ 1)=586.3284 15, calcd for C$_{35}$H$_{44}$N$_3$O$_5$586.328096.

Analysis C$_{35}$H$_{43}$N$_3$O$_5$.0.6 CH$_2$Cl$_2$ C:67.15; H:7.00; N:6.60 Found:(obsd) C:67.05; H:7.00; N:6.55

EXAMPLE 2

Step 1

Preparation of (2S)-N-(1,1-dimethylethoxy-carbonylamino)-1-phenyl-4-penten-3-one, compound 12

To a magnetically stirred solution of vinylmagnesium bromide in THF (0.5 M solution, 122 mL, 61.0 mmol) was added a solution of N',N'-methoxymethyl-N-tert-butyloxy-carbonylphenylalanine carboxamide (4.70 g, 15.24 mmol) in 30 mL THF dropwise over a period of 30 min at –40°≠–25° C. The mixture was stirred for 4 h while the reaction temperature was allowed to warm up to 20° C. When there was no starting material by TLC, 10% citric acid solution (50 mL) was added to the mixture and it was extracted with ethyl ether (2×50 mL) and the ether extracts were combined. The combined organic solution was washed with sat aq NaHCO$_3$ solution (50 mL), water (50 mL), and brine (50 mL), and dried over anhyd MgSO$_4$. Filtered solution was concentrated to give a pale yellow residue, which was used for the next step without further purification. $^1$H NMR (CDCl$_3$) 7.10–7.36 (5H, m), 6.46 (1H, dd, J=9.8, 17.8 Hz), 6.37 (1H, dd, J=1.7, 17.5 Hz), 5.87 (1H, dd, J=1.7, 9.8 Hz), 5.25 (1H, d, J=6.8 Hz), 4.99 (1H, m), 3.17 (1H, A$\underline{B}$X, J$_{AB}$=13.9 Hz, J$_{AX}$=6.4 Hz), 3.01 (1H, A$\underline{B}$X, J$_{AB}$=13.2 Hz, J$_{BX}$=5.6 Hz), 1.44 (9H, s).

Step 2

Preparation of (2S)-N-(1,1-dimethylethoxy-carbonylamino)-3-ethenyl-3(R)-hydroxy-1-phenyl-5-hexene, compound 13

To a magnetically stirred suspension of CeCl$_3$ in THF (50 mL) was added a THF solution of allylmagnesium bromide (1.0 M, 10.25 mL) at 0° C. The mixture was stirred for 1.5 h at 0° C. and the solution turned to deep purple. Compound 12 (1.129 g, 4.10 mmol) in 5 mL THF was dropwise to the reaction mixture at 0° C. and the reaction mixture turned pale yellow. Stirring was continued for 1.5 h at 0° C. Citric acid solution (10% aq. 20 mL) was added to the reaction mixture and it was extracted with ether (2×20 mL). The organic layer was washed with sat aq NaHCO$_3$ solution (20 mL) and brine (20 mL). Drying (over anhyd MgSO$_4$) followed by concentration provided a crude product, which was purified on a silica gel chromatographic column to provide 1.86 g (56%) of compound 13. $^1$H NMR (CDCl$_3$) 7.15–7.32 (5H, m), 5.93 (1H, dd, J=10.7, 17.3 Hz), 5.83 (1H, m), 5.41 (1H, dd, J=1.5, 17.3 Hz), 5.33 (1H, d, J=10.8 Hz), 5.12–5.31 (2H, m), 4.71 (1H, d, J=9.8 Hz), 3.87 (1H, m), 3.06 (1H, A$\underline{B}$X, JAB=14.2, J$_{AX}$=3.2 Hz), 2.59 (1H, A$\underline{B}$X, J$_{AB}$=14.2, J$_{BX}$=11.1 Hz), 2.48 (2H, m), 1.32 (9H, s), 1.16 (1H, br s).

Step 3

Preparation of (4S)-phenylmethyl-3-N-(1,1-dimethylethoxy-carbonyl)-5(R)-ethenyl-5(R)-(2'-propenyl)oxazolidin-2-one compound 14

Compound 14 was prepared in the same manner as compound 5. $^1$H NMR (CDCl$_3$) 7.16–7.32 (5H, m), 5.52–5.70 (2H, m), 5.10–5.34 (4H, m), 4.38 (1H, dd, J=5.7, 7.6 Hz), 2.96 (1H, $\underline{A}$BX, J$_{AB}$=15.0 Hz, J$_{AX}$=5.7 Hz), 2.82 (1H, A$_B$X, J$_{AB}$=15.0 Hz, J$_{BX}$=7.6 Hz), 2.38 (2H, m), 1.43 (9H, s).

Step 4

Preparation of N-(1'(S)-(2'(R)-hydroxyindanyl))-2(S)-(1'-(3'(R)-hydroxy-3'(R)-(1"(S)-tert-butyloxycarbonylamino-2"-phenylethyl)pyrrolidinyl))-3-phenylpropane-amide, compound 16

Compound 16 was prepared from compound 14 in the same manner as compound 7 was prepared from compound 5. mp 82°– 86° C. (dec); $^1$H NMR (CDCl$_3$) 7.12–7.34 (14H, m), 7.04 (1H, d, J=5.9 Hz), 6.63 (1H, d, 7.6 Hz), 5.26 (1H, dd, J=8.7, 5.1 Hz), 5.05 (1H, d, J=9.5 Hz), 4.33 (1H, m), 4.03 (1H, m), 3.41 (1H, m), 3.62 (1H, m), 2.84–3.31 (9H, m), 2.31 (1H, br s), 2.09 (1H, m), 1.86 (1H, m), 1.33 (9H, s);

Analysis calculated for C$_{35}$H$_{43}$N$_3$O$_5$.0.5 CHCl$_3$ C:66.06; H:6.79; N:6.51 Found:(obsd) C:66.28; H:6.96; N:6.18

EXAMPLE 3

Step 1

Preparation of (2S)-N-(1,1-dimethylethoxy-carbonylamino)-1-phenyl-6-hepten-3-one, compound 17

To a magnetically stirred suspension of Mg (6.16 g, 0.254 mol) in ether (200 mL) was added 1-bromo-3-butene (26.31 g, 0.195 mol) dropwise over a period of 30 min. Stirring was continued for 0.5 h. 150 mL THF was added to the solution and the mixture was cooled to –40° C. N',N'-methoxymethyl-N-tert-butyloxycarbonylphenylalanine carboxamide (10.0 g, 32.5 mmol) in THF (10 mL) was added dropwise over a period of 25 min. Stirring was continued for 1.5 h while the flask was allowed to warm up to room temperature. When there was no starting material by TLC, 10% citric acid solution (100 mL) was added to the mixture and it was extracted with ethyl ether (3×50 mL.). Combined organic solution was washed with sat aq NaHCO$_3$ solution (200 mL), and brine (150 mL), and dried over anhyd Na$_2$SO$_4$. Filtered solution was concentrated and the residue was washed with hexane to remove excess 1-bromo-3-butene. After removal of solvents under high vacuum, 6.40 g (65% yield) of compound 13 was obtained as a colorless crystal. $^1$H NMR (CDCl$_3$) 7.12–7.33 (5H, m), 5.73 (1H, m), 5.11 (1H, d, J=7.3 Hz), 4.97 (2H, m), 4.53 (1H, m), 3.05 (1H, A$\underline{B}$X, J$_{AB}$=13.7 Hz, J$_{AX}$=6.6 Hz), 2.95 (1H, A$\underline{B}$X, J$_{AB}$=13.7 Hz, J$_{BX}$=6.3 Hz), 2.47 (2H, m), 2.27 (2H, m), 1.41 (9H, s).

Step 2

Preparation of
(2S)-N-(1,1-dimethylethoxy-carbonylamino)-
3-ethenyl-3(S)-hydroxy-1-phenyl-6-heptene,
compound 18

To a magnetically stirred solution of vinylmagnesium bromide in THF (1.0 M, 63.2 mL) at −40° C. was added a THF solution (20 mL) of (2S)-N-(1,1-dimethylethoxy-carbonylamino)-1-phenyl- 6-hepten-3-one (6.386 g, 21.1 mmol) over a period of 10 min. The mixture was stirred for 1 h while the temperature was allowed to warm up to 15° C. After addition of 10% aq citric acid solution (100 mL), the mixture was diluted with ether (100 mL) and layers separated. The aq layer was extracted with ether (2×50 mL) and the organic layers combined. The combined organic layers were washed with sat aq $NaHCO_3$ solution (2×200 mL) and brine (150 mL). Drying over anhyd $Na_2SO_4$ followed by concentration provided a crude product, which was purified on a silica gel chromatographic column to provide 2.89 g (42% yield) of compound 18. $^1$H NMR ($CDCl_3$) 7.15–7.32 (5H, m), 5.81–5.96 (2H, m), 5.22–5.42 (2H, m), 4.95–5.12 (2H, m), 4.52 (1H, d, J=7.6 Hz), 3.72 (1H, m), 3.13 (1H, ABX, $J_{AB}$=13.0, $J_{AX}$=4.4 Hz), 2.82 (1H, br s), 2.66 (1H, ABX, $J_{AB}$=13.1, $J_{BX}$=11.4 Hz), 2.25 (2H, m), 1.82 (1H, m), 1.67 (1H, m), 1.25 (9H, s).

Step 3

Preparation of
N-(1'(S)-(2'(R)-hydroxyindanyl))-2(S)-
(3'(S)-hydroxy-3'-(1"(S)-tert-butyloxycarbonylamino-
2"-phenyl)ethylpiperidinyl-3-cyclohexylpropaneamide,
compound 19

To a magnetically stirred solution of (2S)-N-(1,1-dimethylethoxy-carbonylamino)- 3-ethenyl-3(S)-hydroxy-1-phenyl-6-heptene (0.196 g, 0.591 mmol) in 5 mL methanol at −78° C. was bubbled in ozone the mixture turned blue. Dimethyl sulfide (0.5 mL) was added at −78° C. and the mixture was warmed to room temperature. Solvent was removed under reduced pressure. The residue was dissolved in methanol (3 mL) and N-tert-butyl-2(S)-amino-3-cyclohexylpropanamide•hydrochloride (0.186 g, 0.710 mmol), $NaCNBH_3$ (0.223 g, 3.55 mmol) and acetic acid (0.081 mL, 1.42 mmol) were added. Stirring was continued for 24 h. The reaction mixture was then partitioned between sat aq $Na_2CO_3$ solution (10 mL) and EtOAc (10 mL) and the aqueous layer was extracted with EtOAc (5 mL×2). Combined organic layers were dried over anhyd $Na_2SO_4$, filtered and concentrated under reduced pressure. The crude product was purified on a silica gel column chromatography (75% EtOAc in hexane) to provide 61.3 mg (20% yield) of compound 19 as a colorless residue. UV (1 max)=259 nm; $^1$H NMR ($CDCl_3$) 7.12–7.32 (5H, m), 6.55 (1H, br s), 4.72 (1H, d, J=8.9 Hz), 3.88 (1H, m), 3.08 (1H, ABX, $J_{AB}$=13.9 Hz, $J_{AX}$=5.1 Hz), 2.82–3.0 (1H, m), 2.63 (1H, ABX, $J_{AB}$=14.0 Hz, $J_{BX}$=11.4 Hz), 2.44–2.7 (3H, m), 2.15–2.30 (1H, m), 1.1–1.85 (17H, m), 1.32 (9H, s), 1.15 (9H, s).

Analysis calculated for $C_{31}H_{51}N_3O_4 \cdot 0.1$ $CHCl_3$ C:68.95; H:9.51; N:7.76 Found:(obsd) C:68.78; H:9.45; N:8.07

EXAMPLE 4

Step 1

Preparation of
(2S)-N-(1,1-dimethylethoxy-carbonylamino)-
3-(2'-propenyl)-3-hydroxy-1-phenyl-5-hexene,
compound 20

Compound 20 was prepared in the same way as compound 4.4. was prepared from compound 3. $^1$H NMR ($CDCl_3$) 7.18–7.32 (5H, m), 5.95 (2H, m), 5.16–5.27 (4H, m), 4.56 (1H, d, J=7.6 Hz), 3.99 (1H, m), 3.12 (1H, ABX, $J_{AB}$=14.5 Hz, $J_{AX}$=3.2 Hz), 2.67 (1H, ABX, $J_{AB}$=14.5 Hz, $J_{BX}$=11.4 Hz), 2.31–2.49 (4H, m), 1.28 (9H, s).

Step 2

Preparation of
N-(1'(S)-(2'(R)-hydroxyindanyl))-2(S)-
(4'(S)-hydroxy-4'(S)-(1"(S)-tert-butyloxycarbonylamino-
2"-phenylethyl)piperidinyl)-3-phenylpropane-amide,
compound 21

Compound 21 was prepared in the same manner from compound 20 as compound 19 from compound LB., 35% yield. mp 193°–195° C.; UV (1 max)=264 nm; $^1$H NMR ($CDCl_3$) 7.15–7.32 (14H, m), 7.09 (1H, d J=6.0 Hz), 5.30 (1H, dd, J=4.9, 8.3 Hz), 4.69 (1H, d, J=8.9 Hz), 3.53 (1H, m), 3.40 (1H, m), 3.26 (1H, ABX, $J_{AB}$=13.6 Hz, $J_{AX}$=8.4 Hz), 2.96–3.24 (3H, m), 2.62–2.89 (7H, m), 2.45 (1 H, br s), 1.59–1.76 (4H, m), 1.31 (9H, s).

Analysis calculated for $C_{36}H_{45}N_3O_5 \cdot 0.12$ $CHCl_3$ C:70.64; H:7.41; N:6.84 Found:(obsd) C:70.68; H:7.50; N:6.75

EXAMPLE 5

Step 1

Preparation of
(2S)-N-(1,1-dimethylethoxy-carbonylsamino)-
5-methyl-1-phenyl-4-hexen-3-one, Compound 22

A THF solution of 2-methyl-1-propenylmagnesium bromide is prepared according to the procedure of D. A. Boyles and D. E. Nichols (*J. Org. Chem.* 1988, 53, 5128–5130). Using the THF solution of 2-methyl-1-propenylmagnesium bromide, compound 22 is prepared (77% yield) in the same manner as compound 12 from compound 2. $^1$H NNMR ($CDCl_3$) 7.10–7.32 (5H, m), 6.08 (1H, s), 5.28 (1H, d, J=6.6 Hz), 4.55 (1H, m), 3.14 (1H, ABX, $J_{AB}$=14.1 Hz, $J_{AX}$=6.5 Hz), 2.98 (1H, ABX, $J_{AB}$=14.6 Hz, $J_{BX}$=5.6 Hz), 2.16 (3H, s), 1.91 (3H, s), 1.43 (9H, s).

Step 2

Preparation of
(2S)-N-(1',1'-dimethylethyloxycarbonyl)amino-
3(R)-hydroxy-3(R)-(2'-methyl-1'-propenyl)-
1-phenyl-6-heptene, Compound 23

Compound 23 is prepared from compound 22 in the smae manner as compound 18 is prepared from compound 17.

Step 3

Preparation of
N-tert-butyl-3-cyclohexyl-2(S)-(3'(R)-hydroxy-
3"(R)-(1"(S)-tert-butyloxycarbonylamino-
2"-phenylethyl)-1'-piperidinyl)propoanamide,
Compound 24

Compound 24 is prepared from compound 23 in the same manner as compound 19 is prepared from compound 18. mp 83°–88.5° C.; $^1$H NMR ($CDCl_3$) 7.18–7.36 (5H, m), 6.68 (1H, br s), 4.65 (1H, d, J=8.8 hz), 3.78 (1H, m), 3.04 (1H, $A_{BX}$, $J_{AB}$=14.0 Hz, $J_{AX}$=5.0 Hz), 3.02 (1H, m), 2.74 (2H, m), 2.72 (1H, $A_{BX}$, $J_{AB}$=14.0 Hz, $J_{BX}$=11.0 Hz), 2.41 (2H, m), 1.20–1.85 (17H, m), 1.41 (9H, s), 1.32 (9H, s).

Analysis calculated for $C_{31}H_{51}N_3O_4 \cdot 0.2\, CHCl_3$ C:67.68; H:9.32; N:7.59 Found:(obsd) C:67.65; H:9.32; N:7.54

While the foregoing specification teaches the principles of the present invention, with examples provided for the purpose of illustration, it will be understood that the practice of the invention encompasses all of the usual variations, adaptations, or modifications, as come within the scope of the following claims and its equivalents.

What is claimed is:

1. A compound of the Formula I

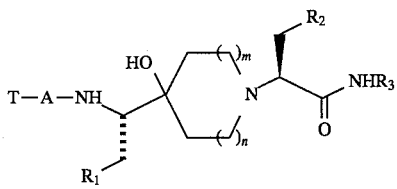

I $m=0,1$;
$n=0,1$;
$R_1$ and $R_2$ are independently
  a) aryl unsubstituted or substituted with one or more of $C_{1-4}$ lower alkyl, hydroxy, $C_{1-3}$ alkoxy or halo;
  b) $C_5-C_7$ cycloalkyl; or
  c) heterocycle unsubstituted or substituted with one or more of $C_{1-4}$ lower alkyl, hydroxy, $C_{1-3}$ alkoxy or halo;
$R_3$ is
  a) hydrogen;
  b) $C_{1-6}$ alkyl, unsubstituted or substituted with one or more of hydroxy, $C_{1-3}$ alkoxy, aryl, heterocycle or halo;
  c) aryl unsubstituted or substituted with one or more of $C_{1-4}$ lower alkyl, hydroxy, $C_{1-3}$ alkoxy or halo;
  d) heterocycle unsubstituted or substituted with one or more of $C_{1-4}$ lower alkyl, hydroxy, $C_{1-3}$ alkoxy or halo; or
  e) a 5 to 7 membered carbocyclic or 7–10 membered bicyclic carbocyclic ring, the carbocyclic ring being unsubstituted or substituted with one or more of $C_{1-4}$ lower alkyl, hydroxy, $C_{1-3}$ alkoxy or halo; and
T is $R_4OC(O)$, $R_4C(O)$ or $R_4NR_5C(O)$ wherein $R_4$ is
  a) $C_{1-5}$ alkyl unsubstituted or substituted with one or more of aryl, heterocycle, hydroxy, halo or $C_{1-3}$ alkoxy;
  b) a 5- to 7-membered carbocycle or carbocycle-$C_{1-4}$ alkyl wherein the carbocycle is either saturated, partially saturated or unsaturated, any of which carbocycle is unsubstituted or substituted with one or more of $C_{1-4}$ alkyl, $C_{2-4}$ alkenyl, $C_{1-3}$ alkoxy, halo-$C_{1-3}$ alkyl, aryl-$C_{1-3}$ alkyl, or $C_{3-5}$ cycloalkyl;
  c) a 5- to 7-membered heterocycle or heterocycle-$C_{1-4}$ alkyl wherein the heterocycle has one or two heteroatoms selected from O, N or S, any of which heterocycle is unsubstituted or substituted with one or more of $C_{1-4}$ alkyl, $C_{2-4}$ alkenyl, oxo, $C_{3-5}$ cycloalkyl, or $C_{1-3}$ alkoxy;
  d) aryl unsubstituted or substituted with one or more of $C_{1-4}$ lower alkyl, hydroxy, $C_{1-3}$ alkoxy or halo; or
  e) heterocycle; and
$R_5$ is
  a) hydrogen, or
  b) $C_{1-4}$ alkyl unsubstituted or substituted with one or more of $C_{2-4}$ alkenyl, $C_{1-3}$ alkoxy, halo-$C_{1-3}$ alkyl, hydroxy-$C_{2-4}$ alkyl, aryl-$C_{1-3}$ alkyl, or $C_{3-5}$ cycloalkyl; and
A is absent or
  a) an L-amino acid residue chosen from valine, isoleucine, leucine, alanine, asparagine or serine; or
  b) 5- to 7-membered heterocycle or heterocycle-$C_{1-4}$ alkyl wherein the heterocycle has one or two heteroatoms selected from O, N or S, any of which heterocycle is unsubstituted or substituted with one or more of $C_{1-4}$ alkyl, $C_{2-4}$ alkenyl, oxo, $C_{3-5}$ cycloalkyl, or $C_{1-3}$ alkoxy, or pharmaceutically acceptable salt thereof.

2. A compound according to claim 1 wherein
A is absent;
T is $R_4OC(O)$;
$R_1$ and $R_2$ are independently phenyl or cyclohexyl, any of which is unsubstituted or substituted with hydroxy or $C_{1-3}$ alkoxy;
$R_3$ is a $C_{1-5}$ alkyl, unsubstituted or substituted with one or more hydroxy or $R_3$ is 1(S)-(2(R)-hydroxyindan); and
$R_4$ is a $C_{1-5}$ alkyl or a 5- to 7-membered heterocycle having one heteroatom selected from O or S, any of which heterocycle is unsubstituted or substituted with one or more of $C_{1-4}$ alkyl, $C_{2-4}$ alkenyl, oxo or $C_{1-3}$ alkoxy.

3. A compound according to claim 2 wherein
T is $R_4OC(O)$;
$R_1$ and $R_2$ are phenyl;
$R_3$ is t-butyl, 2-methylpropyl or 1(S)-(2(R)-hydroxyindan); and
$R_4$ is
  i) $C_{1-5}$ alkyl; or
  ii) 1,1-dioxo-tetrahydrothienyl or tetrahydrofuranyl, unsubstituted or substituted with $C_{1-4}$ alkyl, $C_{2-4}$ alkenyl or $C_{1-3}$ alkoxy.

4. A compound according to claim 3 wherein
$R_4$ is
  i) $C_{1-5}$ alkyl; or
  ii) tetrahydrofuran-3-yl or 1,1-dioxotetrahydrothien-3-yl, unsubstituted or substituted with methyl, ethyl, n-propyl, i-propyl, methoxy, ethoxy, or propenyl.

5. A compound according to claim 1 wherein
$R_1$ and $R_2$ are phenyl;
$R_3$ is 1(S)-(2(R)-hydroxyindan); and
$R_4$ is
  i) $C_{1-5}$ alkyl; or
  ii) a 5- to 7-membered heterocycle having one S heteratom, said heterocycle unsubstituted or substituted with one or more of $C_{1-4}$ alkyl, oxo or $C_{3-5}$ cycloalkyl.

6. A compound according to claim 5 wherein
$R_1$ and $R_2$ are phenyl;
$R_3$ is 1(S)-(2(R)-hydroxyindan); and
$R_4$ is
  i) $C_{1-5}$ alkyl; or
  ii) 1,1-dioxotetrahydrothien-3-yl, unsubstituted or substituted with $C_{1-4}$ alkyl, or $C_{3-5}$ cycloalkyl.

7. The compound:

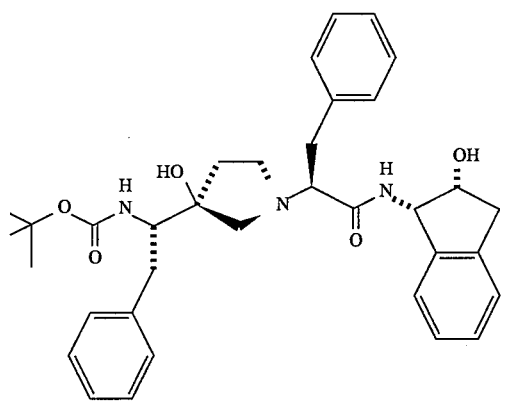

named:

N-(1'(S)-(2'(R)-hydroxyindanyl))-2(S)-(1'-(3'(S)-hydroxy- 3'(S)-(1"(S)-tert-butyloxycarbonylamino-2"-phenylethyl)pyrrolidinyl))- 3-phenylpropane amide;
or pharmaceutically acceptable salt thereof.

8. The compound:

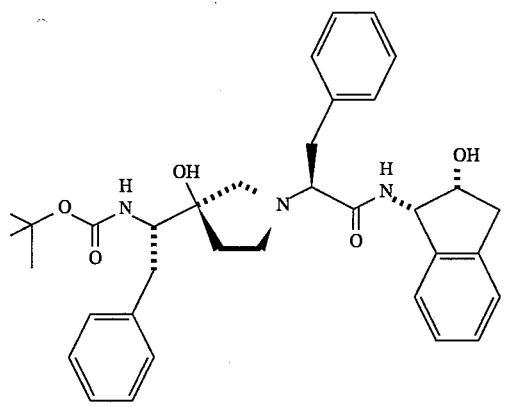

named:

N-(1'(S)-(2'(R)-hydroxyindanyl))-2(S)-(1'-(3'(R)-hydroxy- 3'(R)-(1"(S)-tert-butyloxycarbonylamino-2"-phenylethyl)pyrrolidinyl))- 3-phenylpropane-amide;
or pharmaceutically acceptable salt thereof.

9. The compound:

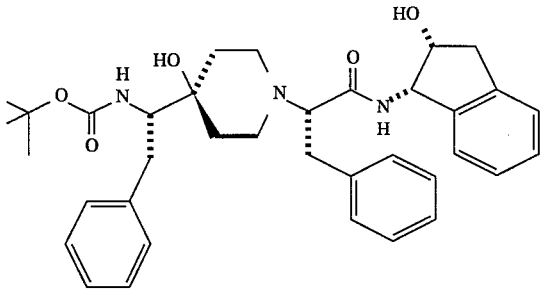

named:

N-(1'(S)-(2'(R)-hydroxyindanyl))-2(S)-(4'(S)-hydroxy-4'(S)-(1"(S)-tert-butyloxycarbonylamino-2"-phenylethyl)piperidinyl)- 3-phenylpropane-amide;
or pharmaceutically acceptable salt thereof.

10. The compound:

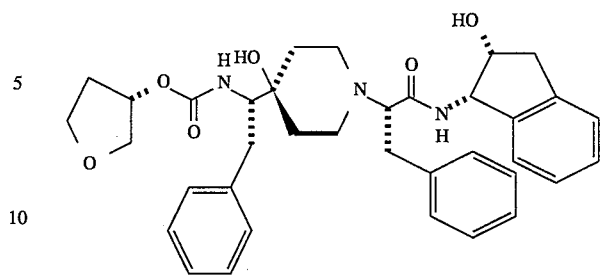

named:

N-(1'(S)-(2'(R)-hydroxyindanyl))-2(S)-(4'-hydroxy-4'(1"(S)-(3'''(S)-tetrahydrofuryloxycarbonyl)amino-2"-phenyl)ethyl- 1'-piperidinyl)-3-phenylpropane-amide;
or pharmaceutically acceptable salt thereof.

11. The compound:

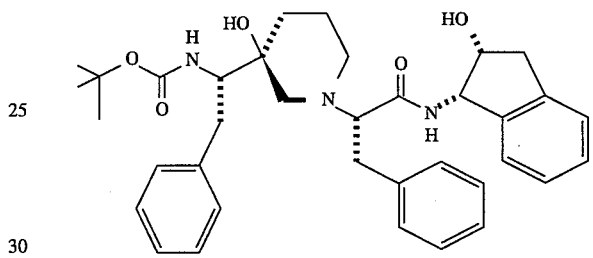

named:

N-(1'(S)-(2'(R)-hydroxyindanyl))-2(S)-(3'(S)-hydroxy-3'(S)-(1"(S)-tert-butyloxycarbonylamino-2"-phenylethyl)- 1'-piperidinyl)-3-phenylpropane-amide;
or pharmaceutically acceptable salt thereof.

12. The compound:

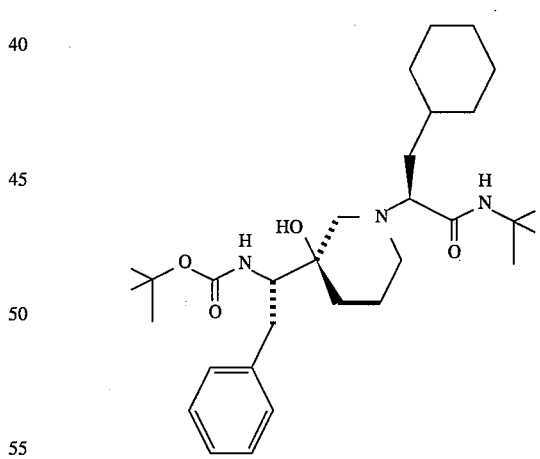

named:

N-(1',1'-dimethylethyl)-2(S)-(3'(R)-hydroxy-3'(R)-(1"(S)-tert-butyloxycarbonylamino-2"-phenylethyl)-1'-piperidinyl)- 3-cyclohexylpropane-amide
or pharmaceutically acceptable salt thereof.

13. A pharmaceutical composition, for use in the treatment of AIDS, in the treatment of infection by HIV, or in the inhibition of HIV protease, comprising an effective amount of a compound as in any of claims 1–12, and a pharmaceutically acceptable carrier.

14. A method of treating AIDS, comprising administering an effective amount of a con, poured as in any of claims 1–12.

15. A method of treating infection by HIV, comprising administering an effective amount of a compound as in any of claims 1–12.

16. A method of inhibiting HIV protease, comprising administering an effective amount of a compound as in any of claims 1–12.

* * * * *